(12) United States Patent
Drahm et al.

(10) Patent No.: US 7,634,939 B2
(45) Date of Patent: Dec. 22, 2009

(54) VISCOMETER

(75) Inventors: Wolfgang Drahm, Erding (DE); Alfred Rieder, Landshut (DE); Christian Matt, Aesch (CH)

(73) Assignee: Endress + Hauser Flowtec AG, Reinach (CH)

( * ) Notice: Subject to any disclaimer, the term of this patent is extended or adjusted under 35 U.S.C. 154(b) by 419 days.

(21) Appl. No.: 10/173,748

(22) Filed: Jun. 19, 2002

(65) Prior Publication Data
US 2008/0127719 A1    Jun. 5, 2008

Related U.S. Application Data

(60) Provisional application No. 60/301,013, filed on Jun. 26, 2001, provisional application No. 60/330,657, filed on Oct. 26, 2001.

(30) Foreign Application Priority Data

Jun. 19, 2001  (EP) ................................. 01114644
Sep. 21, 2001  (EP) ................................. 01122843
Oct. 29, 2001  (EP) ................................. 01125775

(51) Int. Cl.
*G01N 11/10* (2006.01)
(52) U.S. Cl. .................................... 73/54.25
(58) Field of Classification Search ................. 73/54.25
See application file for complete search history.

(56) References Cited

U.S. PATENT DOCUMENTS

| 4,420,753 | A | 12/1983 | Meyer-Ebrecht |
| 4,524,610 | A | 6/1985 | Fitzgerald et al. |
| 4,911,006 | A * | 3/1990 | Hargarten et al. ............. 73/198 |
| 5,869,770 | A * | 2/1999 | Yoshimura et al. ............ 73/861 |
| 5,907,292 | A | 5/1999 | Ahr |
| 6,006,609 | A * | 12/1999 | Drahm et al. .......... 73/861.357 |
| 6,311,136 | B1 | 10/2001 | Henry |
| 6,472,884 | B1 | 10/2002 | Brockhaus |
| 2001/0039829 | A1 | 11/2001 | Wenger |
| 2004/0149650 | A1 | 8/2004 | Hiatt |

FOREIGN PATENT DOCUMENTS

| DE | 27 01 184 A1 | 7/1978 |
| DE | 2701184 A1 | 7/1978 |
| EP | 1 079 213 A2 | 2/2001 |
| EP | 1 094 307 A1 | 4/2001 |
| EP | 1094307 A1 | 4/2001 |
| EP | 1 154 254 A1 | 11/2001 |
| EP | 1154254 A1 | 11/2001 |
| WO | WO 88/02476 | 4/1988 |
| WO | WO 97/12347 | 4/1997 |
| WO | WO 01/29519 A1 | 4/2001 |

* cited by examiner

*Primary Examiner*—John Fitzgerald
(74) *Attorney, Agent, or Firm*—Bacon & Thomas, PLLC (57) ABSTRACT

The viscometer comprises a vibratory transducer with at least one flow tube for conducting a fluid to be measured and for producing friction forces acting in the fluid. To vibrate the at least one flow tube, an excitation assembly is provided, which in operation is traversed by an excitation current. To generate the excitation current and a viscosity value representing the viscosity of the fluid, the viscometer includes meter electronics which are connected to, and supplied with electric power from, a two-wire process control loop. The meter electronics feed a viscosity signal corresponding to the measured viscosity value into the two-wire process control loop. The viscometer is suitable for measuring a fluid flowing in a pipe, particularly in potentially explosive atmospheres.

19 Claims, 9 Drawing Sheets

VISCOMETER

This application is a non-provisional application of provisional application Ser. No. 60/301,013, filed Jun. 26, 2001 and provisional application Ser. No. 60/330,657, filed Oct. 26, 2001.

FIELD OF THE INVENTION

This invention relates to a viscometer for a fluid flowing in a pipe.

BACKGROUND OF THE INVENTION

In measurement and automation technology, the viscosity of a fluid flowing in a pipe, particularly of a liquid, is frequently determined by means of meters which, using a rotary transducer or a vibratory transducer and meter electronics connected thereto, induce internal friction forces in the fluid and derive therefrom a viscosity signal corresponding to the respective viscosity.

Such viscometers and methods of measuring viscosity by means of such meters are described, for example, in U.S. Pat. Nos. 4,524,610, 4,704,898, 4,754,640, 4,920,787, 4,922,745, 5,157,962, 5,228,331, 5,448,921, in WO-A 95/16897, EP-A 527 176 or in EP-A 1 158 289 as well as in European Patent Applications 01 120343.7 and 01 121 869.0, which were not published prior to the filing date of the present application. For generating friction forces acting in the fluid, for example, shear forces, each of these viscometers shown therein comprise an electro-mechanical transducer with a flow tube for conducting the fluid.

In general the in-line viscosimeters as mentioned above could be classified into two groups, firstly viscometers comprising a vibrating or rotating excitation element, for example, a vibrating fork or a rotating cylinder, and secondly viscosmeters with a vibrating flow tube. Latter are described, for example, in U.S. Pat. No. 4,524,610, WO-A 95/16897 or in EP-A 1158289 as well as in the above referred European Patent Applications 01 120343.7 and 01 121 869.0, wherein the viscometers shown therein comprise a vibratory transducer with a flow tube for conducting the fluid, said flow tube communicating with the pipe and vibrating in operation. Each of said vibratory transducers has an excitation assembly for vibrating the flow tube, and a sensor arrangement for sensing vibrations of the flow tube and for generating at least one sensor signal representing the vibrations of the flow tube. Further, the viscometers comprise meter electronics which deliver an excitation current for the excitation assembly and at least one viscosity value representing the instantaneous viscosity of the fluid.

Viscometers of the above type are power-line-operated devices and must therefore have at least two electric leads, i.e., two wires. The viscosity signal, which is preferably proportional to the viscosity of the fluid, is produced and output according to a standard established for this purpose, such as the 4- to 20-mA current standard and/or a usual frequency standard and/or a digital standard; for this, at least two further wires are necessary.

SUMMARY OF THE INVENTION

Particularly if several such viscometers are used in a plant and/or if viscometers are installed at a location remote from the external power supply, the use of additional line material will entail considerable expense. Furthermore, in measurement and automation technology, there is a need for standardized or at least substantially uniform interfaces between such meters and, e.g., coordinating control units. It is also desirable to keep the variety of such interfaces as small as possible.

To attain these objects, the invention provides a viscometer for a fluid flowing in a pipe, said viscometer comprising:

a vibratory transducer, particularly a flexural and/or a torsional mode transducer, with at least one flow tube for conducting the fluid, and for generating friction forces acting in the fluid, the at least one flow tube communicating with the pipe and vibrating in operation, and with an excitation assembly for vibrating the at least one flow tube; and meter electronics which have a predeterminable electric power requirement and deliver an excitation current for the excitation assembly and a viscosity value representing the instantaneous viscosity of the fluid, said meter electronics being connected to, and supplied with electric power from, a two-wire process control loop, and said meter electronics feeding and controlling, respectively, a viscosity signal corresponding to the viscosity value into the two-wire process control loop.

In a first embodiment of the invention, the electric power requirement of the meter electronics is variable, and the meter electronics comprise a control circuit for adjusting the electric power requirement.

In a second embodiment, the meter electronics comprise an excitation circuit for generating the excitation current; and an evaluating circuit for registering the sensor signal and for determining the viscosity value, with the control circuit temporarily deactivating the excitation circuit and/or the evaluating circuit to reduce the electric power requirement.

In a third embodiment of the invention, the meter electronics comprise an energy store which is coupled to the two-wire process control loop and by which the power required by the meter electronics is made available at least in part and/or at least temporarily.

According to a further development of the third embodiment, the control circuit causes temporary charging of the energy store.

In a fourth embodiment of the invention, the viscometer is connected by means of the two-wire process control loop to a field bus.

In a fifth embodiment of the invention, the two-wire process control loop carries a direct current; in that case, the viscosity signal is preferably a variable direct current, particularly a current in a range of 4 to 20 mA, or preferably a digital signal.

In a sixth embodiment of the invention, the transducer comprises a sensor arrangement for sensing vibrations of the flow tube and for producing at least one sensor signal representing said vibrations.

According to a development of the sixth embodiment, the meter electronics adjust the excitation current by means of the sensor signal.

According to a further development of the sixth embodiment, the excitation circuit comprising an demodulation stage fed by one of the sensor signals or a sum of both sensor signals, said demodulation stage being operable to generate an output signal representing an oscillation amplitude of said vibrating tube, a comparison stage fed by the output signal of the demodulation stage, said comparison stage being operable to generate an output signal representing a deviation of said oscillation amplitude of the vibrating tube from an predetermined reference oscillation amplitude for said vibrations. In a first variant of this development the excitation circuit further comprising an amplitude modulation stage for modulating said signal fed to the demodulation stage with said output signal from the comparison stage, said amplitude stage being operable to generate a drive signal for supplying said excitation assembly. In a second variant of the this development the excitation circuit further comprising an pulse duration modulation stage for modulating said signal fed to the demodulation stage with said output signal from the comparison stage, said pulse duration stage being operable to generate a drive signal for supplying said excitation assembly.

The invention is based on surprising recognition that the minimum electric power transmitted over two-wire process control loops alone suffices for the operation of conventional viscometers with a vibrating measuring tube. It has also been found that in most fields of application, the viscosity to be measured varies with time only so slightly that low-frequency updating of the measured viscosity value and, thus, only temporary operation of the meter are possible.

Furthermore, the time distance between the updatings of the measured viscosity value can be readily made so great— or, in other words, the updating frequency can be chosen to be so low—that even if the power transmitted over the two-wire process control loop should temporarily be insufficient to meet the power requirement of the viscometer, an energy store can be charged, so that the required power can be kept available in the meter electronics.

Through the invention, a marketable two-wire viscometer is provided for the first time; this is a basic advantage of the invention. The two wires serve both to supply the required power, for which purpose an external power source, generally a DC source, has to be connected to the two wires, and to transmit the output current, i.e., the viscosity signal in this invention.

Preferably, the two-wire viscometer is so designed that the output current flowing in the two wires represents, and particularly is proportional to, a signal generated by means of a physical-to-electrical transducer. In the case of this invention, the physical-to-electrical transducer is the at least one flow tube, and the output current is the viscosity signal. In the case of two-wire meters according to the above-mentioned 4- to 20-mA current standard, a given current value within this current range corresponds to exactly one output signal value, i.e., to exactly one value of the viscosity signal in this invention. Only the current range below 4 mA is usable for the supply of power to the electronics of the two-wire viscometer. As a result, the power supply only makes available power on the order of 50 mW, which will hereinafter be referred to as "low power". In view of these facts, a two-wire viscometer with the aforementioned 4- to 20-mA current standard is particularly suited for use in potentially explosive atmospheres, so that such a two-wire viscometer can meet the requirements of the various classes of explosion protection.

Furthermore, the two-wire viscometer can be designed in a simple manner to be capable of cooperating with one of the conventional field buses. This can be accomplished by connecting the meter to the field bus directly, e.g., according to the Fieldbus protocol (Fieldbus is a registered trademark of Fieldbus Foundation), or indirectly via a bus coupler. e.g., according to the so-called HART protocol (HART is a registered trademark of the HART User Group).

BRIEF DESCRIPTION OF THE DRAWINGS

Further advantages of the invention and the invention itself will now be explained in more detail with reference to the accompanying drawings, which show preferred embodiments of the invention. Parts having similar functions are designated by similar reference characters throughout the various figures of the drawings, but these reference characters are repeated in subsequent figures only if this appears appropriate. In the drawings.

DETAILED DESCRIPTION OF EXEMPLARY EMBODIMENTS

While the invention is susceptible to various modifications and alternative forms, exemplary embodiments thereof have been shown by way of example in the drawings and will herein be described in detail. It should be understood, however, that there is no intent to limit the invention to the particular forms disclosed, but on the contrary, the intention is to cover all modifications, equivalents, and alternatives falling within the spirit and scope of the invention as defined by the intended claims.

Figure 1:
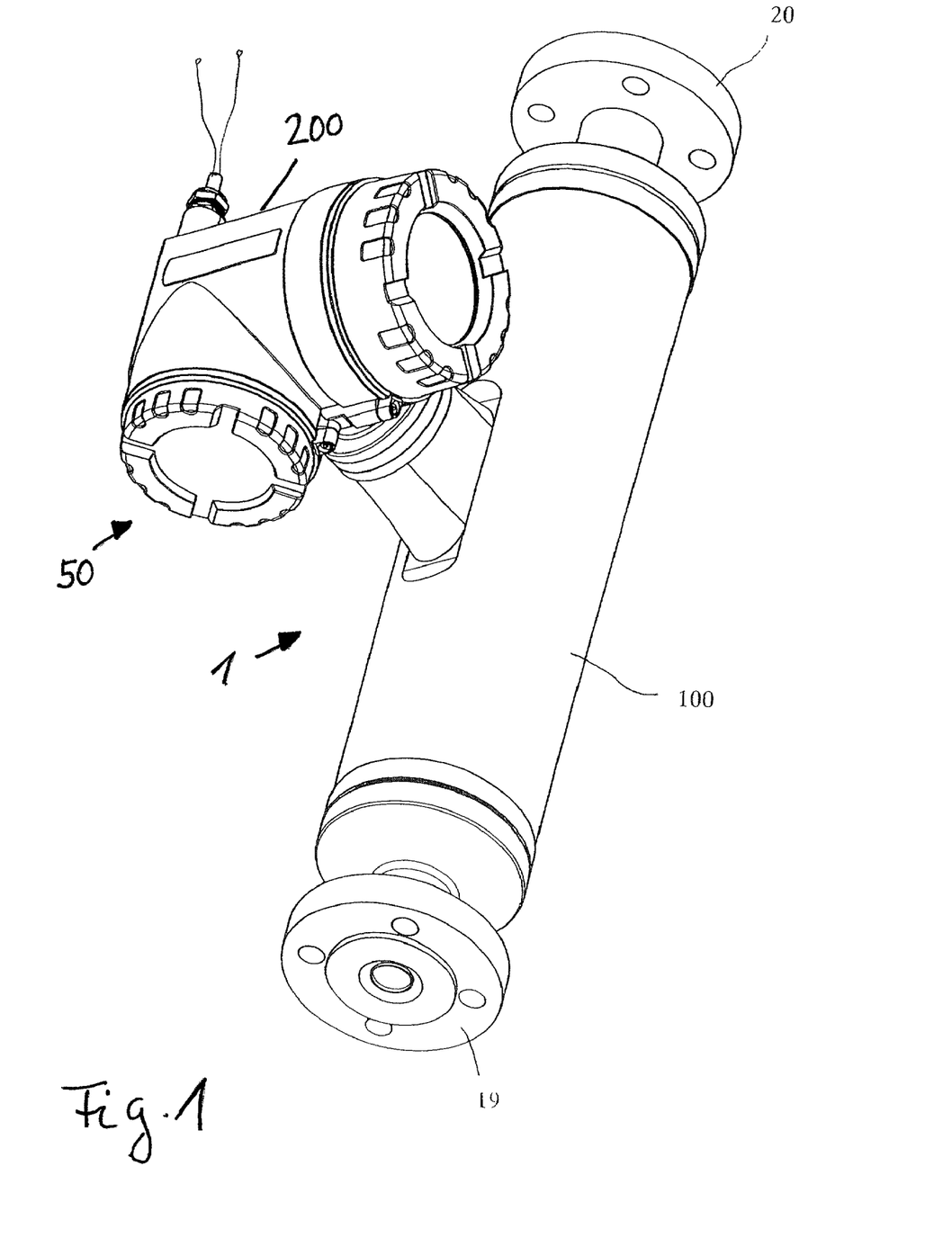
FIG. 1 is a perspective view of a viscometer for indicating a viscosity value.

FIG. 1 shows a viscometer 1 with a vibratory transducer, preferably housed in a transducer case 100, and with meter electronics 50, housed in an electronics case 200 and electrically connected to transducer; meter electronics 50 are described in detail below.

Viscometer 1 serves to sense a viscosity of a fluid flowing in a pipe and to convert this viscosity into a viscosity value X; the pipe is not shown for the sake of clarity. By means of the transducer, which is excited into vibration by meter electronics 50, friction forces are generated in the fluid passing therethrough which are dependent on the viscosity η and which react on the transducer in a measurable manner, i.e., which can be detected using sensor technology and converted into useful input signals for subsequent evaluation electronics.

Figure 2:
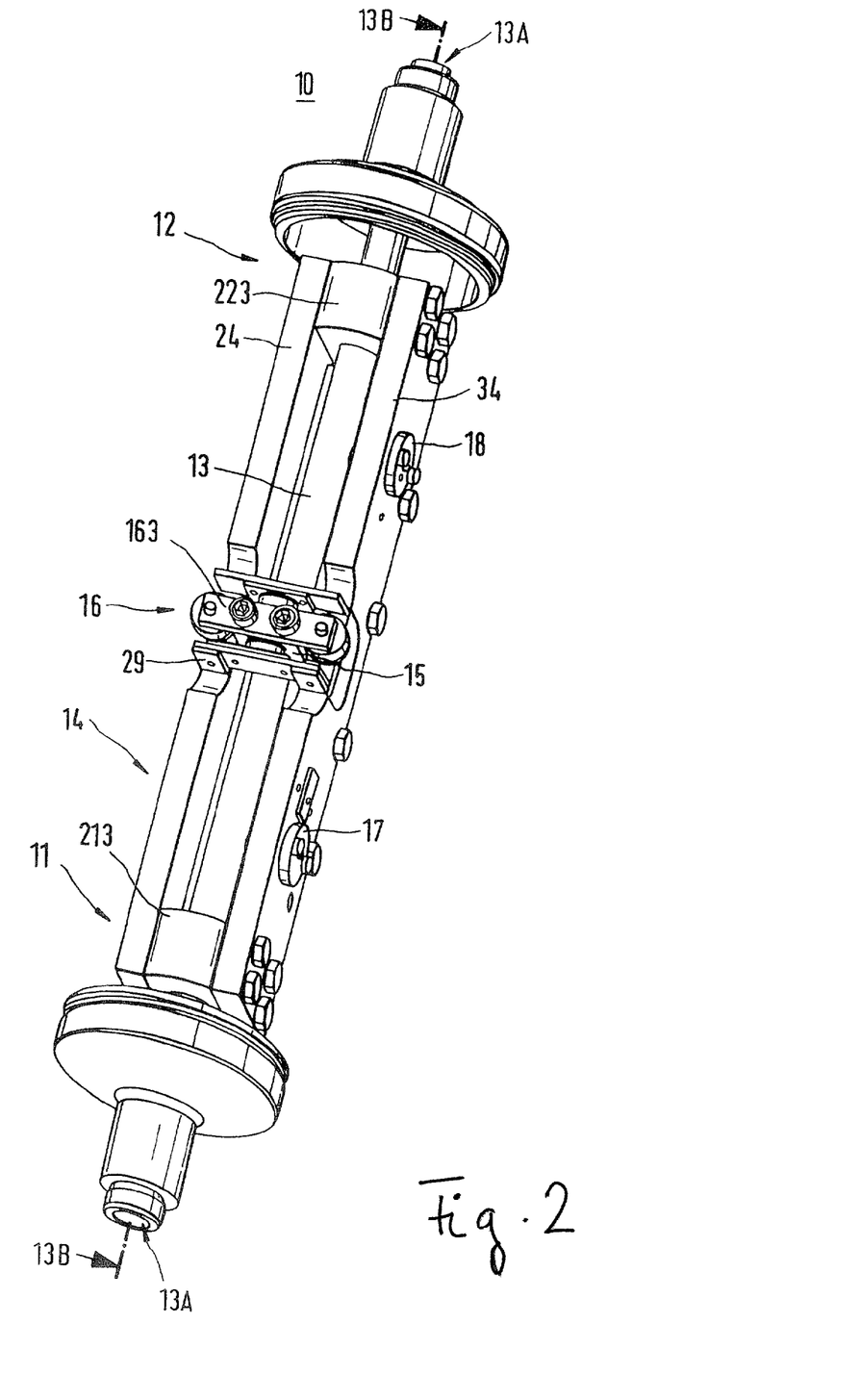
FIG. 2 is a part-sectional, first perspective view of an embodiment of a vibratory transducer suitable for the viscometer of FIG. 1.
Figure 3:
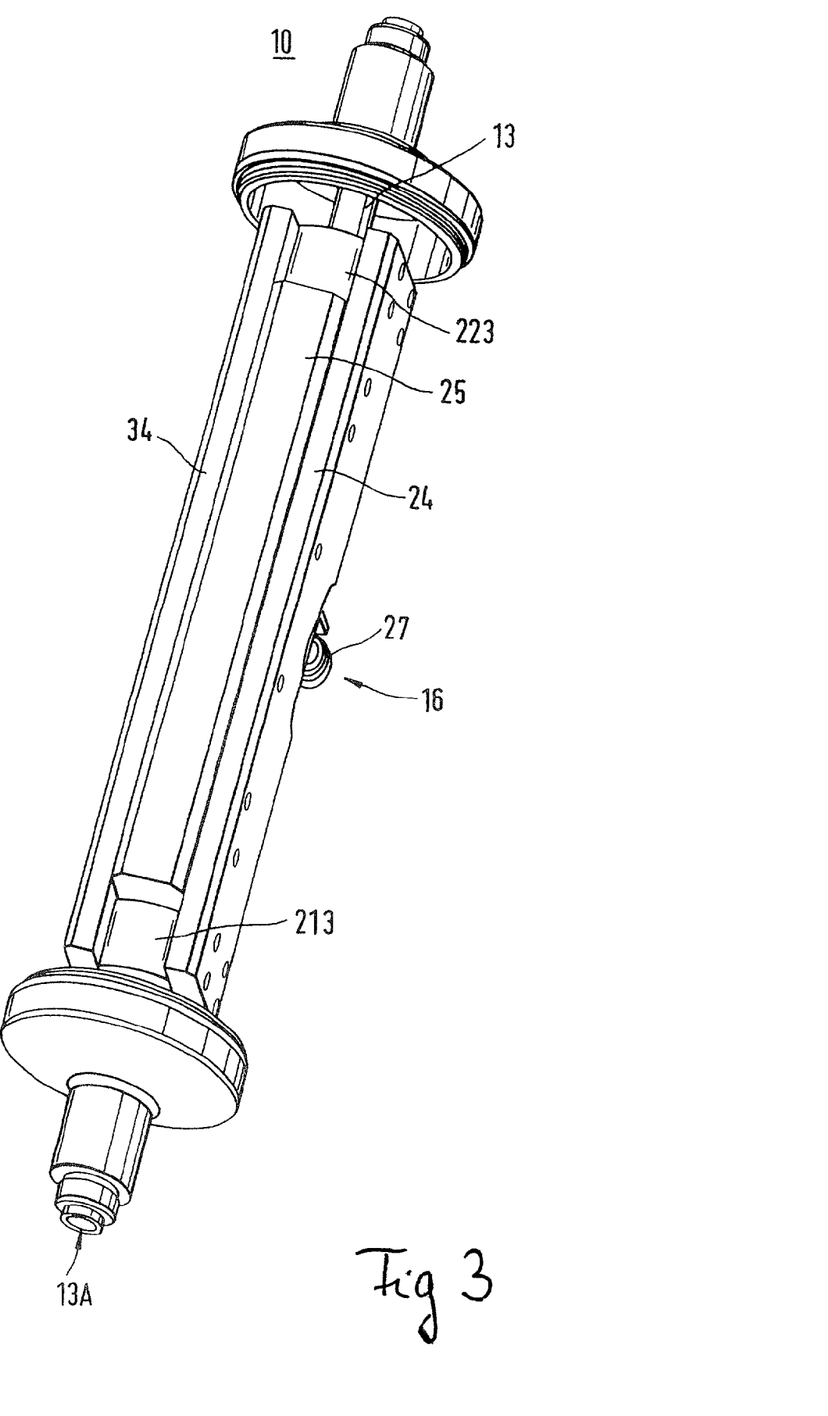
FIG. 3 is a second perspective view of the transducer of FIG. 2.

FIGS. 2 and 3 show an embodiment of a transducer 10 in the form of a physical-to-electrical vibratory transducer assembly. The construction of such a transducer assembly is described in detail in U.S. Pat. No. 6,006,609, for example, but for the measurement of other flow variables.

To conduct the fluid to be measured, transducer 10 comprises at least one flow tube 13 of a predeterminable, elastically deformable lumen 13A and a predeterminable nominal diameter, which has an inlet end 11 and an outlet end 12.

"Elastic deformation of lumen 13A" as used herein means that in order to produce reaction forces in the fluid, i.e., forces describing the fluid, namely shearing or friction forces of transducer 10, in operation, a three-dimensional shape and/or a spatial position of lumen 13A are changed in a predeterminable cyclic manner, particularly periodically, within an elasticity range of flow tube 13; see, for example, U.S. Pat. No. 4,801,897, U.S. Pat. No. 5,648,616, U.S. Pat. No. 5,796,011, and/or U.S. Pat. No. 6,006,609.

At this point is should be noted that instead of a transducer according to the embodiment of FIGS. 2 and 3, virtually any of the prior-art transducers for the aforementioned other flow variables, particularly a flexural mode transducer with a bent or straight flow tube vibrating exclusively or at least in part in a flexural mode, can be used for implementing the invention.

Further suitable implementations of transducer assemblies that can be used for transducer 10 are described, for example, in U.S. Pat. No. 5,301,557, 5,357,811, 5,557,973, 5,602,345, 5,648,616, or 5,796,011, which are incorporated herein by reference.

Materials especially suited for flow tube 13, which is straight in FIGS. 2 and 3, are titanium alloys, for example. Instead of titanium alloys, other materials commonly used for such flow tubes, particularly for bent tubes, such as stainless steel or zirconium, may be employed.

Flow tube 13, which communicates at the inlet and outlet ends with the fluid-conducting pipe in the usual manner, is clamped in a rigid support frame 14, particularly in a flexurally and torsionally stiff frame, so as to be capable of vibratory motion, the support frame being preferably enclosed by a transducer case 100.

Support frame 14 is fixed to flow tube 13 by means of an inlet plate 213 at the inlet end and by means of an outlet plate 223 at the outlet end, the two plates being penetrated by respective corresponding extension pieces of flow tube 13. Support frame 14 has a first side plate 24 and a second side plate 34, which are fixed to inlet plate 213 and outlet plate 223 in such a way as to extend essentially parallel to and in spaced relationship from flow tube 13; see FIG. 2. Thus, facing side surfaces of the two side plates 24, 34 are also parallel to each other.

Figure 4:
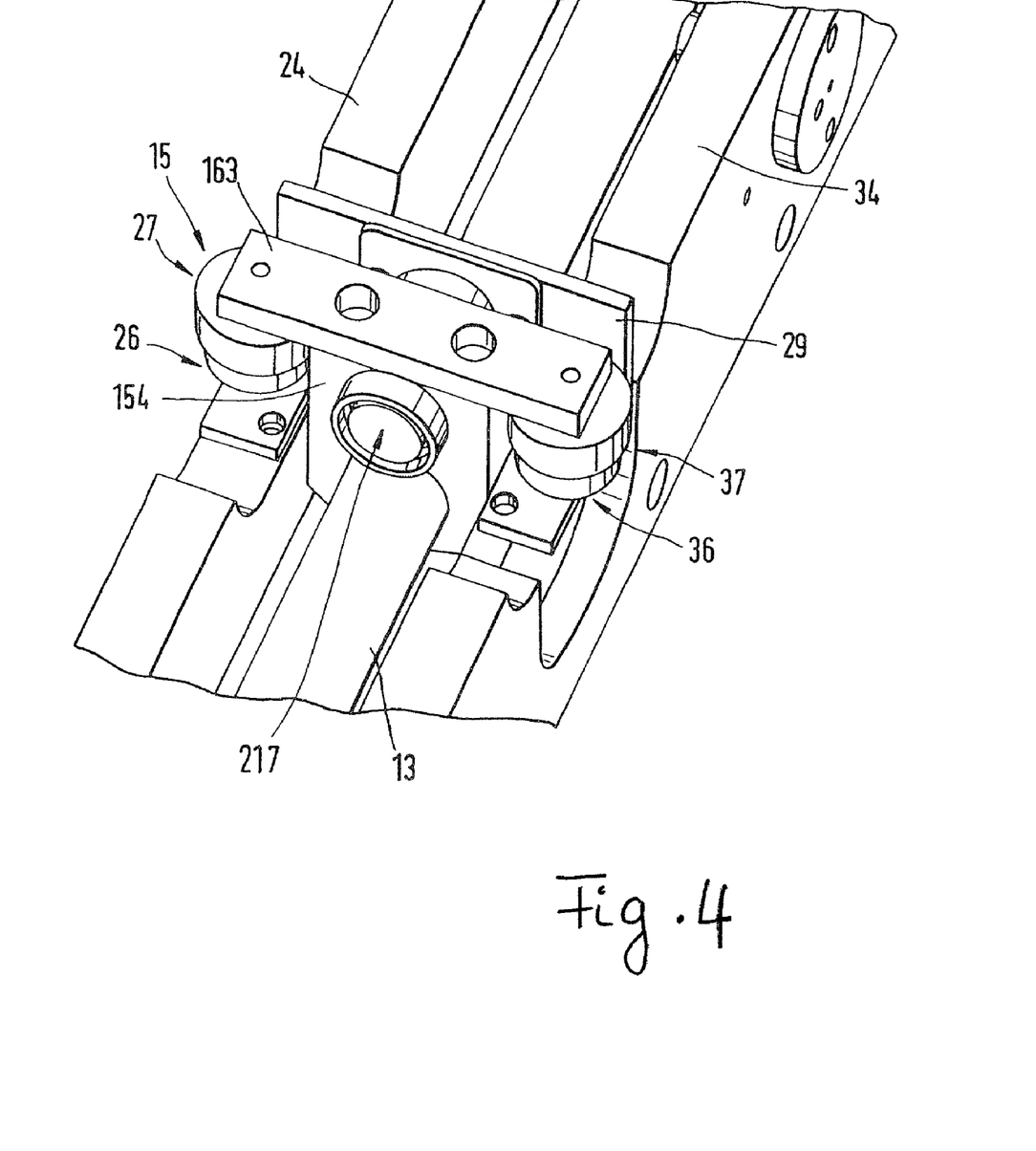
FIG. 4 shows an embodiment of an electromechanical excitation assembly for the transducer of FIG. 2.

A longitudinal bar 25 serving as a balancing mass for absorbing vibrations of flow tube 13 is secured to side plates 24, 34 in spaced relationship from flow tube 13. As shown in FIG. 4, longitudinal bar 25 extends essentially parallel to the entire oscillable length of flow tube 13; this, however, is not mandatory; if necessary, longitudinal bar 25 may also be shorter, of course.

Thus, support frame 14 with the two side plates 24, 34, inlet plate 213, outlet plate 223, and the optional longitudinal bar 25 has a longitudinal axis of gravity which is essentially parallel to a central flow tube axis 13B, which joins inlet end 11 and outlet end 12.

In FIGS. 2 and 3, it is indicated by the heads of the screws shown that the aforementioned fixing of side plates 24, 34 to inlet plate 213, to outlet plate 223 and to longitudinal bar 25 may be done by screwing; it is also possible to use other suitable forms of fastening familiar to those skilled in the art.

If transducer 10 is to be nonpermanently connected with the pipe, flow tube 13 preferably has an inlet-side first flange 19 and an outlet-side second flange 20 formed thereon, see FIG. 1; instead of flanges 19, 20, other pipe couplings, such as the so-called Triclamp connections indicated in FIG. 2, may be used to provide the nonpermanent connection with the pipe. If necessary, however, flow tube 13 may also be connected with the pipe directly, e.g., by welding or brazing.

To produce the above-mentioned friction forces, during operation of transducer 10, flow tube 13, driven by an electromechanical excitation assembly 16 coupled to the flow tube, is caused to vibrate in the so-called useful mode at a predeterminable frequency, particularly at a natural resonance frequency, whereby the flow tube is elastically deformed in a predeterminable manner; it should be noted that this resonance frequency is also dependent on the density of the fluid.

In the embodiment shown, the vibrating flow tube 13, as is usual with such flexural mode transducer assemblies, is spatially, particularly laterally, deflected from a static rest position; the same applies to transducer assemblies in which one or more bent flow tubes perform cantilever vibrations about a corresponding longitudinal axis joining the respective inlet and outlet ends, or to those in which one or more straight flow tubes perform only planar flexural vibrations about their longitudinal axis.

If transducer 10 is a radial mode transducer assembly and the cross section of the vibrating flow tube is symmetrically deformed in the usual manner as is described, for example, in the above-mentioned WO-A 95/16897, the longitudinal flow tube axis will remain in its static rest position.

Excitation assembly 16 serves to produce an excitation force $F_{exc}$ acting on flow tube 13 by converting an electric excitation power $P_{exc}$ supplied from meter electronics 50. The excitation power $P_{exc}$ serves virtually only to compensate the power component lost in the vibrating system because of mechanical and fluid friction. To achieve as high an efficiency as possible, the excitation power $P_{exc}$ is preferably precisely adjusted so that essentially the vibrations of flow tube 13 in the useful mode, e.g., those at a fundamental resonance frequency, will be sustained.

For the purpose of transmitting the excitation force $F_{exc}$ to flow tube 13, excitation assembly 16, as shown in FIG. 4, has a rigid, electromagnetically and/or electrodynamically driven lever arrangement 15 with a cantilever 154 and a yoke 163, the cantilever 154 being rigidly fixed to flow tube 13. Yoke 163 is rigidly fixed to an end of cantilever 154 remote from flow tube 13, such that it lies above and extends transversely of flow tube 13.

Cantilever 154 may be a metal disk, for example, which receives flow tube 13 in a bore. For further suitable implementations of lever arrangement 15, reference is made to the above-mentioned U.S. Pat. No. 6,006,609. As is readily apparent from FIG. 2, lever arrangement 15, here a T-shaped arrangement, is preferably arranged to act on flow tube 13 approximately midway between inlet end 11 and outlet end 12, so that in operation, flow tube 13 will exhibit its maximum lateral deflection in the middle.

To drive the lever arrangement 15, excitation assembly 16, as shown in FIG. 4, comprises a first excitation coil 26 and an associated first armature 27 of permanent-magnet material as well as a second excitation coil 36 and an associated second armature 37 of permanent-magnet material. The two excitation coils 26 and 36, which are preferably electrically connected in series, are fixed to support frame 14 on both sides of flow tube 13 below yoke 163, particularly nonpermanently, so as to interact in operation with their associated armatures 27 and 37, respectively. If necessary, the two excitation coils 26, 36 may, of course, be connected in parallel.

As shown in FIGS. 2 and 4, the two armatures 27, 37 are fixed to yoke 163 at such a distance from each other that during operation of transducer 10, armature 27 will be penetrated by a magnetic field of excitation coil 26, while armature 37 will be penetrated by a magnetic field of excitation coil 36, so that the two armatures will be moved by the action of corresponding electrodynamic and/or electromagnetic forces.

The motions of armatures 27, 37 produced by the magnetic fields of excitation coils 26, 36 are transmitted by yoke 163 and cantilever 154 to flow tube 13. These motions of armatures 27, 37 are such that yoke 163 is displaced from its rest position alternately in the direction of side plate 24 and in the direction of side plate 34. A corresponding axis of rotation of lever arrangement 15, which is parallel to the above-mentioned central axis 13B of flow tube 13, may pass through cantilever 154, for example.

Particularly in order to hold excitation coils 26, 36 and individual components of a magnetic brake assembly 217, which is mentioned below, support frame 14 further comprises a holder 29 for electromechanical excitation assembly 16. Holder 29 is connected, preferably nonpermanently, with side plates 24, 34.

In the transducer 10 of the embodiment, the lateral deflections of the vibrating flow tube 13, which is firmly clamped at inlet end 11 and outlet end 12, simultaneously cause an elastic deformation of its lumen 13A; this elastic deformation extends virtually over the entire length of flow tube 13.

Furthermore, due to a torque acting on flow tube 13 via lever arrangement 15, torsion is induced in flow tube 13 about central axis 13B simultaneously with the lateral deflections, at least in sections of the tube, so that the latter vibrates in a mixed flexural and torsional mode serving as the useful mode.

The torsion of flow tube 13 may be such that the direction of a lateral displacement of the end of cantilever 154 remote from flow tube 13 is either the same as or opposite to that of the lateral deflection of flow tube 13. Thus, flow tube 13 can perform torsional vibrations in a first flexural and torsional mode, corresponding to the former case (same direction), or in a second flexural and torsional mode, corresponding to the latter case (opposite direction). In the transducer 10 according to the embodiment, the fundamental resonance frequency of the second flexural and torsional mode, e.g., 900 Hz, is approximately twice as high as that of the first flexural and torsional mode.

If flow tube 13 is to perform vibrations only in the second flexural and torsional mode, excitation assembly 16 will advantageously incorporate a magnetic brake assembly 217 based on the eddy-current principle, which serves to stabilize the position of the axis of rotation. By means of magnetic brake assembly 217 it can thus be ensured that flow tube 13 always vibrates in the second flexural and torsional mode, so that any external interfering effects on flow tube 13 will not result in a spontaneous change to another flexural and torsional mode, particularly to the first. Details of such a magnetic brake assembly are described in detail in U.S. Pat. No. 6,006,609.

At this point it should be mentioned that in the flow tube 13 thus deflected according to the second flexural and torsional mode, the central axis 13B is slightly deformed, so that during the vibrations, this axis spreads a slightly curved surface rather than a plane. Furthermore, a path curve lying in this surface and described by the midpoint of the central axis of the flow tube has the smallest curvature of all path curves described by this central axis.

To detect the deformations of flow tube 13, transducer 10 comprises a sensor arrangement 60 with at least a first sensor 17, which provides a first, preferably analog, sensor signal s1 in response to vibrations of flow tube 13. Sensor 17 may be formed, for example, by an armature of permanent-magnet material fixed to flow tube 13 and interacting with a sensor coil held by support frame 14.

Sensor types especially suited for sensor 17 are those which sense the velocity of the deflections of flow tube 13 based on the electrodynamic principle. It is also possible to use acceleration-measuring electrodynamic or displacement-measuring resistive or optical sensors, or other sensors familiar to those skilled in the art which are suitable for detecting such vibrations.

Sensor arrangement 60 further comprises a second sensor 18, particularly a sensor identical to the first sensor 17, which second sensor 18 provides a second sensor signal s2 representing vibrations of flow tube 13. In this embodiment, the two sensors 17, 18 are positioned at a given distance from each other along flow tube 13, particularly at the same distance from the middle of flow tube 13, such that sensor arrangement 60 will detect both inlet-side and outlet-side vibrations of flow tube 13 and provide corresponding sensor signals s1 and s2 respectively.

Figure 5:
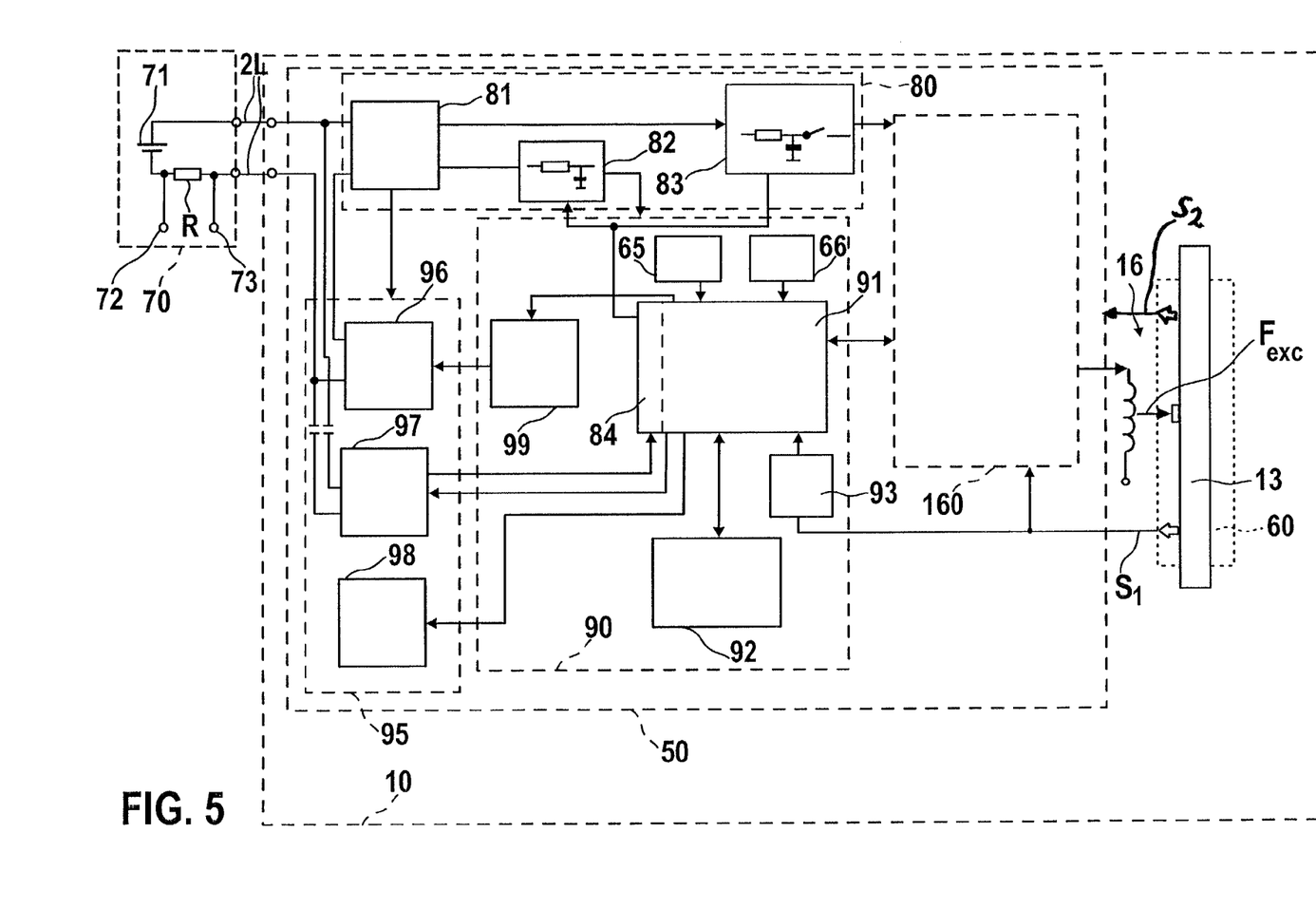
FIG. 5 shows schematically in block-diagram form a preferred embodiment of meter electronics suitable for the viscometer of FIGS. 1 to 4.

The first sensor signal s1 and, if present, the second sensor signal s2 which usually each have a frequency corresponding to the instantaneous vibration frequency of flow tube 13, are fed to meter electronics 50, as shown in FIG. 5.

To vibrate the flow tube 13, excitation assembly 16 is supplied from meter electronics 50 with a likewise oscillating excitation current $i_{exc}$ of adjustable amplitude and adjustable frequency $f_{exc}$, such that in operation, excitation coils 26, 36 are traversed by this current to produce the magnetic field necessary to move armatures 27, 37. The excitation current $i_{exc}$ is a sinusoidal current.

In this embodiment, the frequency $f_{exc}$ of the excitation current $i_{exc}$ is chosen and adjusts itself so that the laterally vibrating flow tube 13 vibrates, if possible exclusively, in the second flexural and torsional mode.

FIG. 5 shows schematically in block-diagram form a preferred embodiment of meter electronics 50 suitable for the viscometer of FIGS. 1 to 4. The flow tube 13, the excitation assembly 16, and the sensor arrangement 60 are depicted schematically on the right, with excitation coil 26 represented by its symbol; it is connected to circuit ground SN of the viscometer 1.

Meter electronics 50 are framed in Fig. S by dashed lines. They are connected to a two-wire process control loop 2L, hereinafter referred to as a loop for the sake of brevity. The loop 2L runs from viscometer 1 to a process control room 70, for example. There it is connected to a series combination of an external power source, e.g., a DC source, which feeds a loop current into loop 2L, and a shunt R; the latter is provided with two test terminals 72, 73, across which the viscosity signal can be taken as a voltage drop, which can be indicated or applied to subsequent signal processing circuits. Power source 71 thus provides meter electronics 50 with the power necessary for its operation. If loop 2L operates according to the 4- to 20-mA current standard, which has been used in industrial measurement technology for a long time, the current range between 0 and 3.6 mA will be available for the supply of power.

Within meter electronics 50, the two wires of loop 2L are connected to a voltage regulator 81 which generates a sufficiently constant voltage from the generally varying output voltage of supply source 71. This constant voltage is fed permanently or intermittently to all subcircuits of meter electronics 50, see below.

To supply excitation assembly 16 with the aforementioned excitation current $i_{exc}$, meter electronics 50 comprise an excitation circuit 160; preferred embodiments of this circuit are explained with reference to FIGS. 6 to 11. At this point it suffices to mention that the output signal s1 of sensor 17 is fed to excitation circuit 160.

As shown in FIG. 5, excitation circuit 160 is also in contact with a microprocessor 91 of an evaluating circuit 90, from which the excitation circuit 160 receives the necessary operating data or to which the excitation circuit 160 sends internally generated adjustment signals and/or parameters, particularly information about the adjusted excitation current $i_{exc}$ and/or the excitation power $P_{exc}$ injected into the transducer. In addition to or in place of microprocessor 91, evaluating circuit 90 may contain a digital signal processor for generating measurement and operating data.

The measurement and operating data generated and/or received by evaluating circuit 90 may be stored in a volatile data memory 92, for example.

In a preferred embodiment of the invention, the sensor signal s1 is also fed directly to evaluating circuit 90. There, the signal, after being digitized by an analog-to-digital converter 93, is applied to the microprocessor and/or signal processor 91, which provides the viscosity value Xη. Microprocessor and/or signal processor 91 has a system clock generator 66 and a watchdog and reset stage 65 associated with it.

By means of a current regulator 96, which is preceded by a digital-to-analog converter 99 fed by the digital viscosity value Xη, meter electronics 50 modulate the viscosity value Xη onto the amplitude of the current flowing in loop 2L. In other words, by adjusting the amplitude of the loop current in accordance with the instantaneous viscosity value Xη, meter electronics 50 feeds a viscosity signal corresponding to the measured viscosity value Xη into loop 2L.

In another preferred embodiment of the invention, meter electronics 50 further include a communication interface 97 which serves to convert the viscosity value Xη and, e.g., internal meter parameters into signals transmissible over loop 2L and couple these signals into the latter, and to receive meter parameters transmitted from outside the meter via loop 2L. The communication interface 97 may be, for example, an interface according to the HARTS field communications protocol of HART® Communication Foundation, Austin Tex., which uses FSK-coded, higher-frequency alternating voltages as signal carriers.

In a further preferred embodiment of the invention, meter electronics 50 include at least one energy store coupled to loop 2L; in FIG. 5, two of them can be seen, namely energy stores 82, 83. With such an energy store, the power required by meter electronics 50 can be made available at least in part and/or at least temporarily, particularly if the power currently made available by loop 2L does not suffice to operate the meter electronics 50.

Energy store 82 is constantly connected to both voltage regulator 81 and evaluating circuit 90, so that it is charged and discharged as required. By contrast, energy store 83 is connected to excitation circuit 160 through a switch with which the discharge can be interrupted.

In a further preferred embodiment of the invention, the electric power requirement of meter electronics 50, i.e., its power consumption, is variable and can thus be adapted to the currently available electric power. The variation of the power requirement of meter electronics 50 may be controlled in accordance with the currently available power or by means of clock pulses, for example. To control the power consumption, meter electronics 50 therefore include a control circuit 84, which may be implemented with the microprocessor and/or signal processor 91, for example.

The control of the electric power requirement may be accomplished by arranging, for example, that control circuit 84 temporarily deactivates excitation circuit 160 and/or evaluating circuit 90 for reducing the power consumption.

"Deactivating the evaluating circuit 90" means, for example, that the latter is changed to a state of low power consumption in which at least the functions required to control the energy store or reactivate the evaluating circuit are left in operation and in which the measurement data and/or operating parameters necessary for the operation of evaluating circuit 90 after its reactivation are kept available in a data memory, e.g., in volatile data memory 92. The excitation circuit may also be deactivated by being fully turned off, for example.

Figure 6:
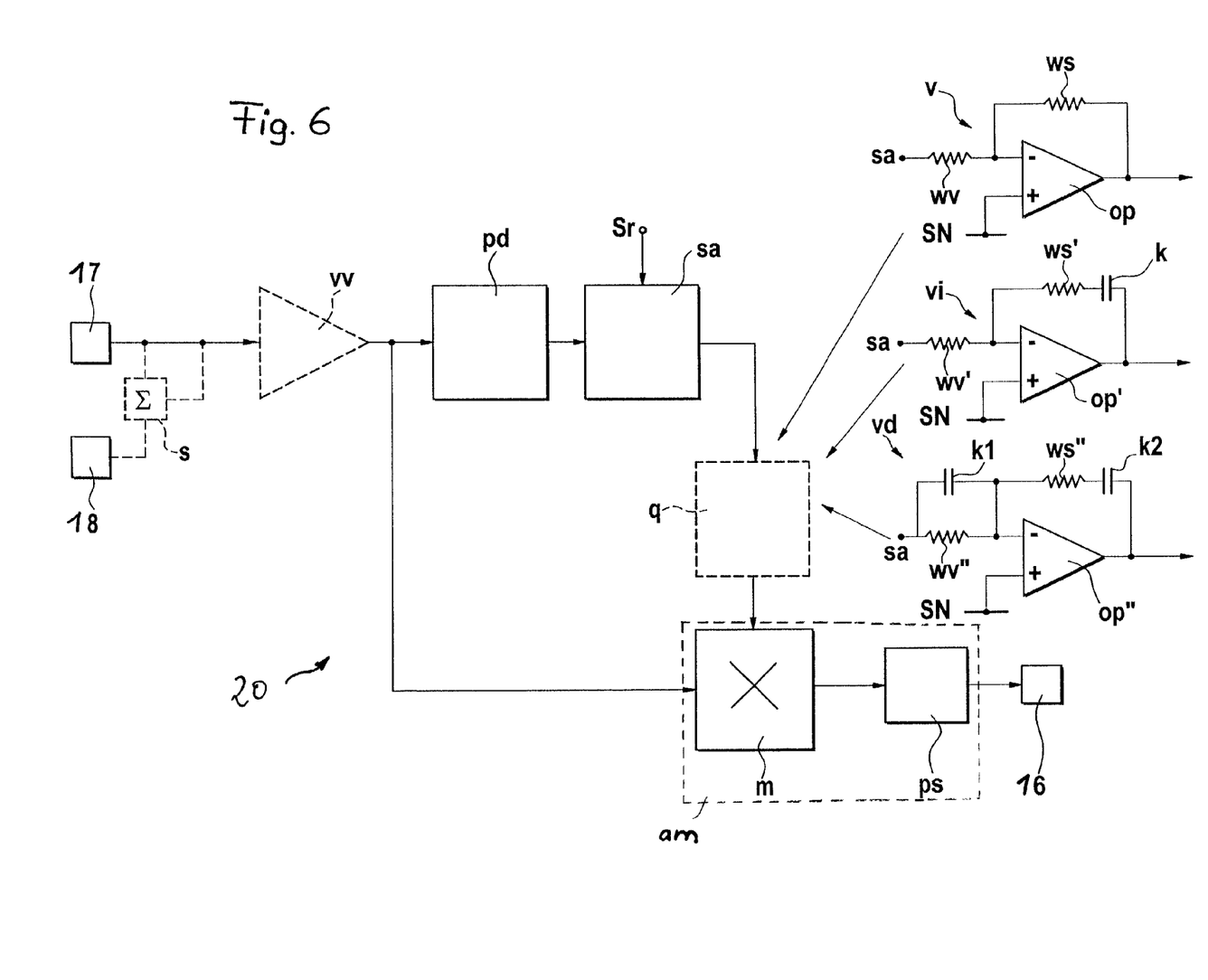
FIG. 6 shows partly in block-diagram form the circuit diagram of an embodiment of a first preferred excitation circuit.

FIG. 6 shows, partly in block-diagram form, the circuit diagram of an embodiment of excitation circuit 20 according to the first variant of the invention. A demodulation stage pd receives one of the sensor signals or their sum as its input signal. Consequently, demodulation stage pd has its input connected to one of the velocity or displacement sensors, henceforth called "sensors" for short; in FIG. 6, this is sensor 17. The demodulation stage serves to determining an oscillation amplitude of tube vibrations. Further, the stage pd is operable to generate an output signal representing said detected oscillation amplitude of the vibrating tube. Therefore, in a preferred embodiment of the invention the demodulation stage pd comprises a peak detector for said input signal. Instead of a peak detector a lock-in amplifier which is clocked by a reference signal being in phase with the input signal may be used for detecting the amplitude of the input signal of the demodulation stage pd.

A first input of a comparison stage sa is connected to an output of demodulation stage pd; a second input of comparison stage sa is fed an adjustable reference signal Sr which specifies an amplitude of the vibration of flow tubes 1, 2. Compairion stage sa determines a deviation of the output signal of demodulation stage pd from the reference signal Sr. This deviation may be determined as an absolute error by using a simple difference between the detected amplitude and the predetermined amplitude specified by the reference signal Sr, or as an relative error by using a ratio of the detected and the predetermined amplitudes.

A first input of an amplitude modulation stage am receives the input signal to demodulation stage pd, and a second input receives the output signal from comparison stage sa. The amplitude modulation stage am serves to modulate said input signal of the demodulation stage with the output signal from the comparison stage. For these purposes, in a preferred embodiment the amplitude modulation stage am comprises a simple multiplier circuit m, as shown in FIG. 7.

The sensor signal or the sum of the two sensor signals—or a respective signal proportional thereto, see below—is the carrier signal, and the output signal from comparison stage sa is the modulating signal, which is—at least slowly—varying; it represents the deviation of the instantaneous vibration amplitude of the flow tube or of flow tubes 1, 2 from the vibration amplitude specified by reference signal Sr.

Furthermore, the amplitude modulation stage am is operable to generate a drive signal supplying the excitation assembly 16. Thus, amplitude stage am comprises a output stage ps for amplifying said input signal being modulated with said output signal from the comparison stage.

Figure 7:
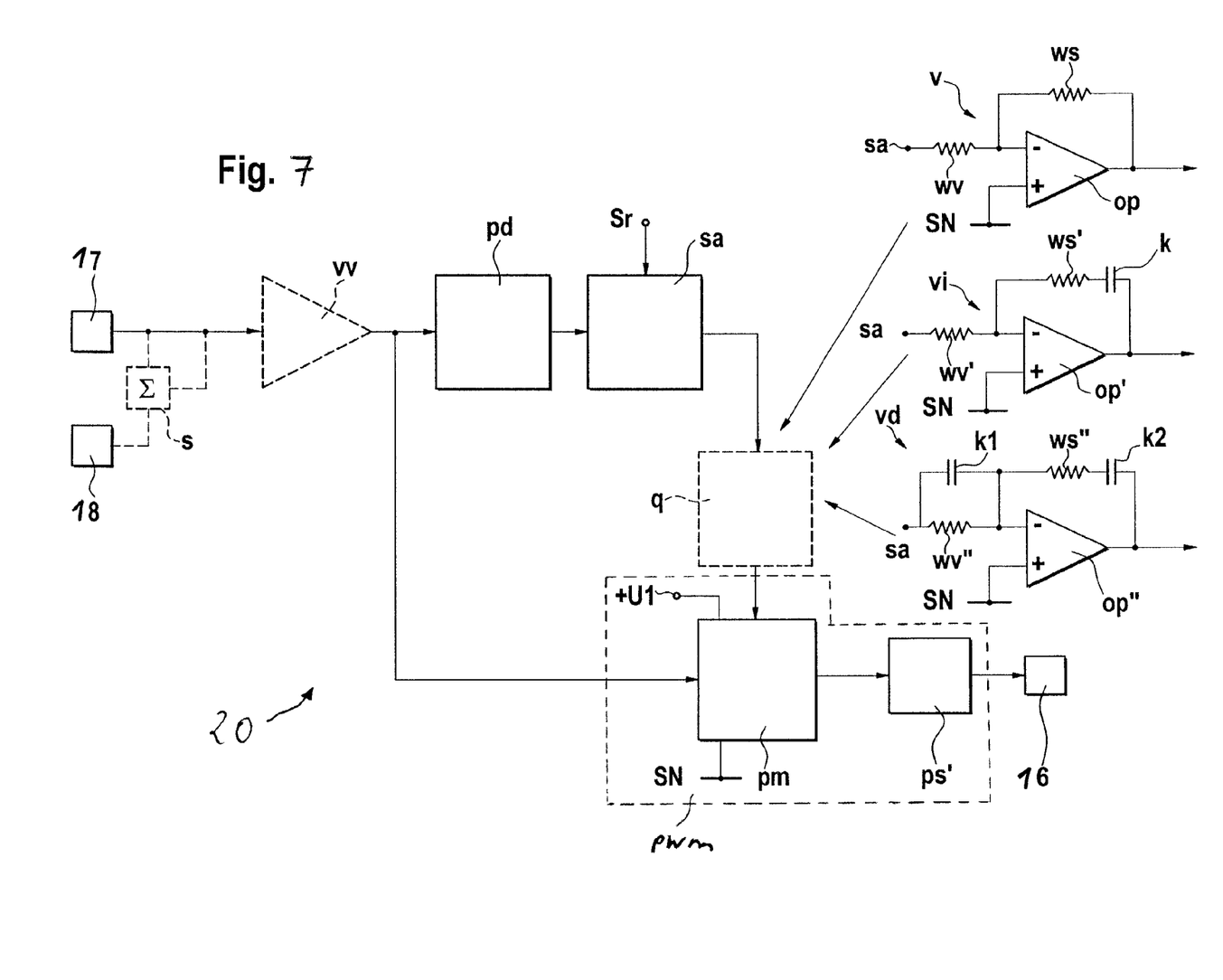
FIG. 7 shows partly in block-diagram form the circuit diagram of an embodiment of a second preferred excitation circuit.

FIG. 7 shows, partly in block-diagram form, the circuit diagram of an embodiment of excitation circuit 20 according to the second variant of the invention. The embodiment of FIG. 7 differs from that of FIG. 6 in that the amplitude modulation stage am of FIG. 6 has been replaced by a pulse width modulation stage pwm comprising a puls duration modulator pm being clocked by an external AC-signal. Pulse duration modulator pm, shown in FIG. 7, operates on a constant positive first DC voltage +U1 and is connected to ground SN.

A first input of puls duration modulator pm—this is the carrier signal input—receives the input signal of demodulation stage pd. Thus, this first input is connected to one of the sensors; in FIG. 7, this is again sensor 17.

A second input of puls duration modulator pm—this is the modulating-signal input—receives the output signal from comparison stage sa. The output of pulse duration modulator pm is adjusted by an output stage ps' which delivers a drive signal for excitation assembly 16. This drive signal being a square wave signal clocked with a signal frequency of the input signal of demodulation stage pd and having pulse width modulated with the output signal from comparison stage sa.

Figure 8:
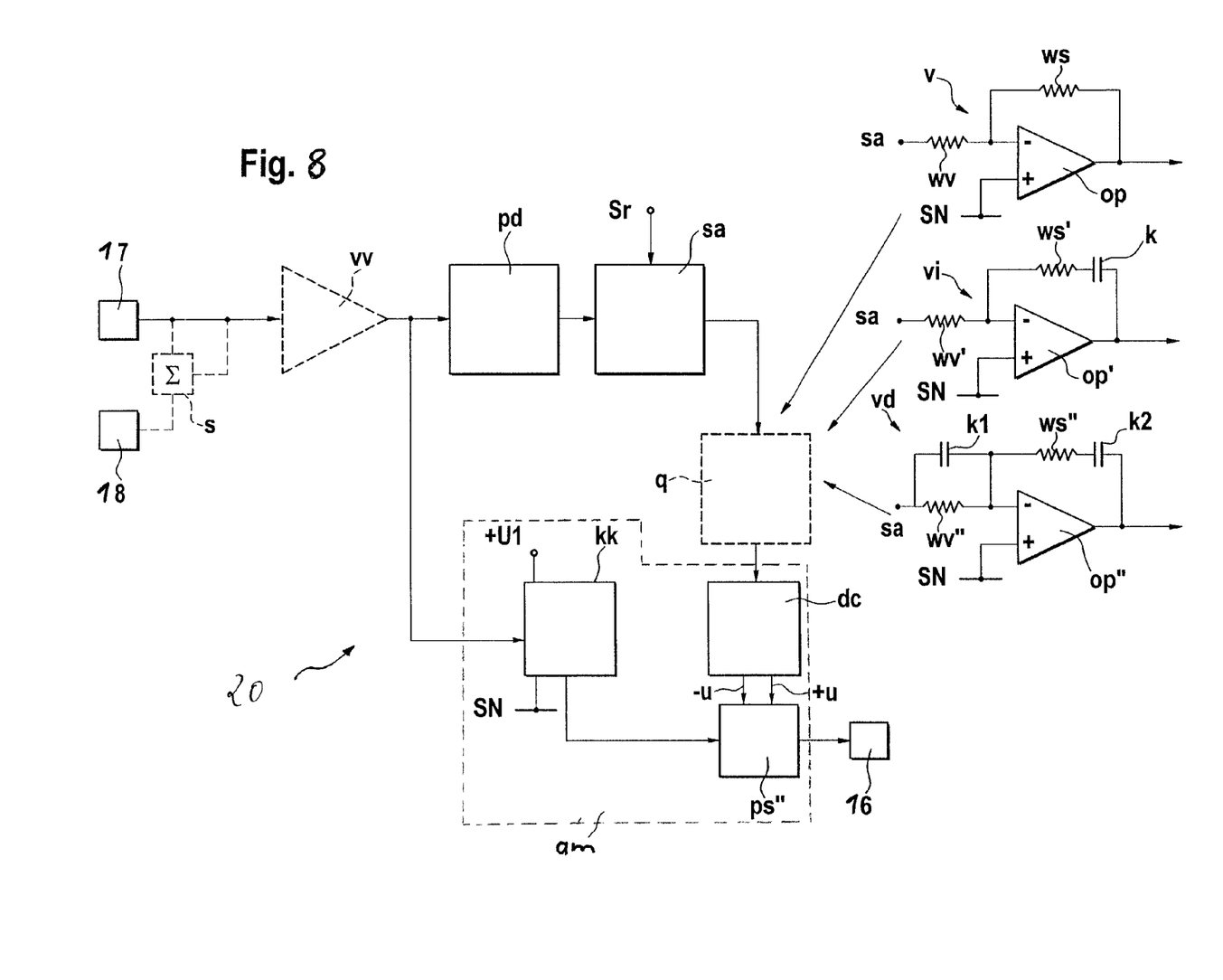
FIG. 8 shows partly in block-diagram form the circuit diagram of an embodiment of a third preferred excitation circuit.

FIG. 8 shows, partly in block-diagram form, the circuit diagram of an embodiment of excitation circuit 20 according to the third variant of the invention. The embodiment of FIG. 8 differs from that of FIG. 6 in that the multiplier m of FIG. 6 has been replaced by a comparator kk and a DC/DC converter DC which delivers at least one supply voltage for driving a switched excitation current in the excitation assembly 16.

The amplitude of the supply voltage depends on the output signal from comparison stage sa and must therefore be regarded as non-constant. Depending on this supply voltage the excitation current may be a bi-polar, or an uni-polar current.

Therefore, in the embodiment as shown in FIG. 8 the DC/DC converter DC delivers supply voltage having a positive first potential +u and a negative second potential −u. A control input of DC/DC converter dc receives the output signal from comparison stage sa. An output stage ps'' is connected at the input end to an output of comparator kk; it is supplied with the potentials +u, −u provided by DC/DC converter dc, and supplies excitation assembly 16. Comparator kk operates on a constant DC voltage +U1 and is connected to ground SN. An input of comparator kk receives the input signal to peak detector pd. Thus, comparator kk is connected at the input end to one of the sensors; in FIG. 8, this is again sensor 17.

In FIGS. 5 to 8 it is indicated by broken lines that instead of one of the signals from sensors 17, 18, the sum of these signals may be fed to peak detector pd and to multiplier m or pulse duration modulator pm or comparator kk; in that case, these sensor signals must be passed through a summer s.

FIGS. 5 to 8 include further subcircuits represented by broken lines, which constitute preferred developments of the excitation circuit of the invention.

In a development the amplitude modulation stage am is provided with a preamplifier vv for the input signal. The preamplifier vv may be connected ahead of the peak detector and the lock-in amplifier, respectively.

In a development of the excitation circuit 20 an amplifier v amplifies the output signal from comparison stage sa before it is applied to multiplier m. Such an amplifier may be an operational amplifier op whose noninverting input is connected to ground SN and whose inverting input is connected via a dropping resistor wv to the output of comparison stage sa and via a shunt resistor ws to the amplifier output. The operational amplifier wired in this way, op, can be seen in FIGS. 5 to 8 on the upper right.

In a further development of the excitation circuit 20 an integrating amplifier vi amplifies and integrates the output signal from comparison stage sa before it is applied to multiplier m. Such an amplifier may be an operational amplifier op' whose noninverting input is connected to ground SN and whose inverting input is connected via a dropping resistor wv' to the output of comparison stage sa and via a series combination of a shunt resistor ws' and a capacitor k to the amplifier output. The operational amplifier wired in this way, op', can be seen in FIGS. 5 to 8 on the right-hand side in the middle.

In another development of the excitation circuit 20 a differentiating and integrating amplifier vd amplifies, differentiates, and integrates the output signal from comparison stage sa before it is applied to multiplier m. Such an amplifier may be an operational amplifier op'' whose noninverting input is connected to ground SN and whose inverting input is connected via a parallel combination of a dropping resistor wv'' and a first capacitor k1 to the output of comparison stage sa and via a series combination of a shunt resistor ws'' and a second capacitor k2 to the amplifier output. The operational amplifier wired in this way, op'', can be seen in FIGS. 5 to 8 on the lower right.

The arrows in FIGS. 5 to 8 indicate that the respective amplifier v, vi, vd has to be put in the place of the square q represented by broken lines, which is located either between the output of comparison stage sa and the second input of amplitude modulation stage am, or between the output of comparison stage sa and the modulating-signal input of pulse width modulation stage pwm, respectively.

It is within the scope of the invention that the functions of the individual subcircuits of FIGS. 5 to 8 are implemented with suitable analog or digital subcircuits, i.e., in the latter case with a suitably programmed microprocessor, for example, in which case the signals to be applied to the latter have to be subjected to an analog-to-digital conversion, while its output signals may have to be subjected to a digital-to-analog conversion.

Figure 9:
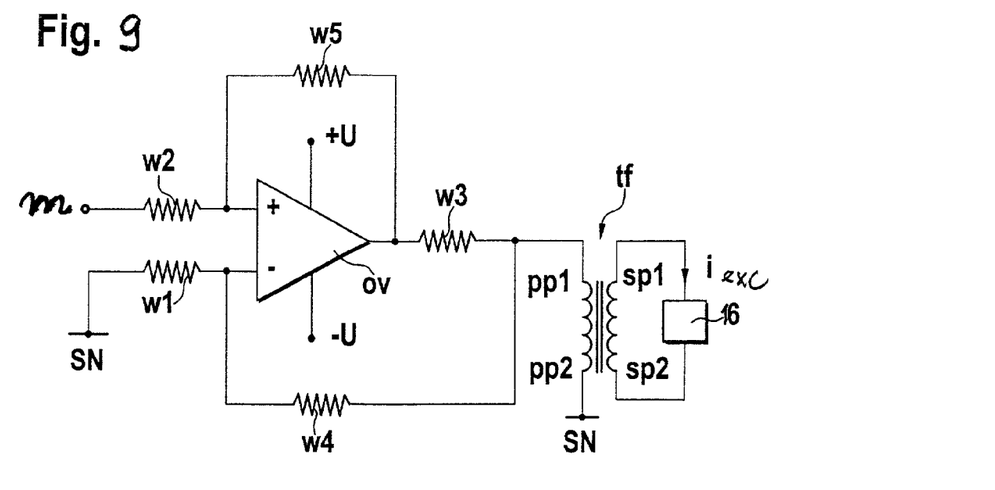
FIG. 9 is a circuit diagram of an embodiment of a preferred output stage of the excitation circuit of FIG. 6.

FIG. 9 is a schematic circuit diagram of a first preferred embodiment of an output stage ps provided in the amplitude modulation stage am, which is shown in FIG. 6.

An operational amplifier ov operates on a positive constant DC voltage +U and a negative constant DC voltage −U and is wired as follows. An inverting input is connected through a first resistor w1 to ground SN, and a noninverting input is connected through a second resistor w2 to the output of multiplier m.

An output of operational amplifier ov is connected via a third resistor w3 to a first terminal pp1 of a primary winding of a transformer if; a second terminal pp2 of the primary winding is connected to ground SN. Transformer ff also has a secondary winding, whose two terminals sp1, sp2 are connected to excitation assembly 16.

The primary winding has a number of turns N1, and the secondary winding has a number of turns N2. Transformer if is a step-up transformer and has a turns ratio N1/N2 of, e.g., 20:1.

The inverting input of operational amplifier ov is connected via a fourth resistor w4 to the first terminal pp1 of the primary winding. The noninverting input is connected via a fifth resistor w5 to the output.

The five resistors w1, w2, w3, w4, w5 have respective resistance values R1, R2, R3, R4, R5. Value R1 must be chosen to be equal to value R2, and value R4 must be chosen to be equal to value R5. If $u_m$ is the output voltage of multiplier m, the alternating current i flowing in excitation assembly 16 is given by $$i = u_m \cdot \frac{R5}{R1 \cdot R3} \cdot \frac{N1}{N2}$$

Figure 10:
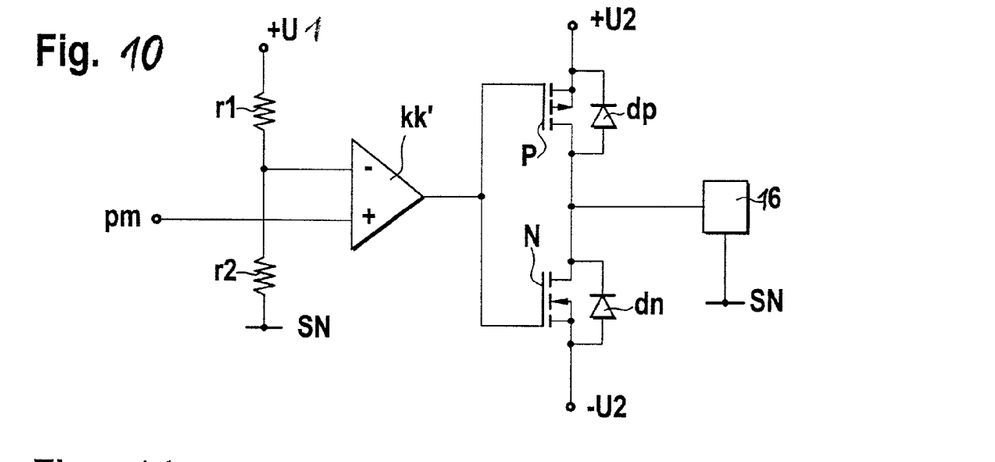
FIG. 10 is a circuit diagram of an embodiment of a preferred output stage of the excitation circuit of FIG. 7.

FIG. 10 is a schematic circuit diagram of a second preferred embodiment of an output stage ps' provided in the pulse duration modulation stage pwm, which is shown in FIG. 7.

The "core" of this embodiment of output stage ps', which is a complementary push-pull stage, is a series combination of the controlled current paths of a P-channel enhancement-mode insulated-gate field-effect transistor P and an N-channel enhancement-mode insulated-gate field-effect transistor N, hereinafter referred to as transistors for short.

Excitation assembly 16 is connected to the junction point of the controlled current paths. Each controlled current path is shunted by a protective diode dn, dp, with the respective cathode connected to the more positive point of the respective transistor.

The P-transistor-side end of the series combination is connected to a constant positive second DC voltage +U2, and its N-transistor-side end is connected to a corresponding negative DC voltage −U2. The gates of transistors N, P are connected together and to an output of a comparator kk'. The noninverting input of comparator kk' is connected to the output of pulse duration modulator pm, see FIG. 7.

The inverting input of comparator kk' is connected to a tap of a voltage divider consisting of a resistor r1 and a resistor r2. Resistors r1, r2 are of equal value and are connected between the positive DC voltage +U1 and ground SN. Resistors r1, r2 and comparator kk' serve to balance the output signal of pulse duration modulator pm with respect to half the value of the DC voltage +U1.

Thus, excitation assembly 16 receives a positive current pulse on each positive-going zero crossing of the output signal from sensor 17 or of the sum of the output signals from sensors 17, 18, and a negative current pulse on each negative-going zero crossing of the output signal from sensor 17 or of the sum of the output signals from sensors 17, 18. The respective duration of these current pulses adjusts itself automatically so that the vibration amplitude of the flow tube or of flow tubes 1, 2 specified by reference signal Sr is reached.

Figure 11:
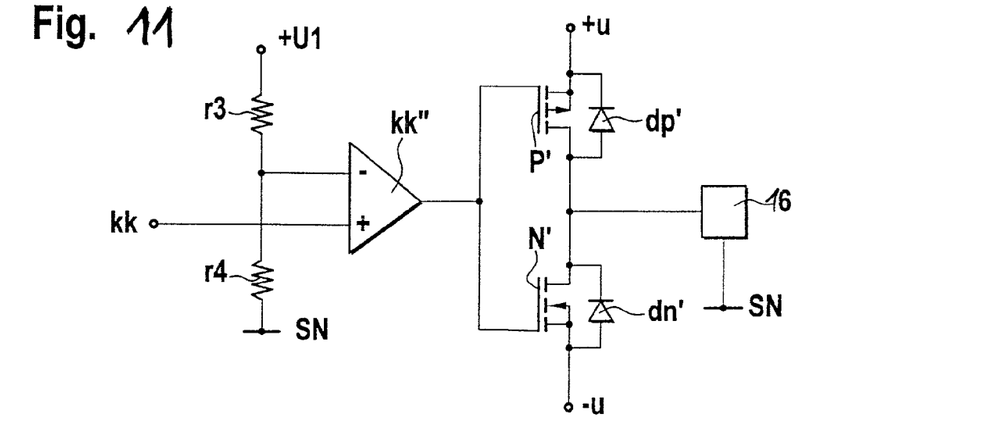
FIG. 11 is a circuit diagram of an embodiment of a preferred output stage of the excitation circuit of FIG. 8.

FIG. 11 is a schematic circuit diagram of a third preferred embodiment of an output stage ps" provided in the amplitude modulation stage am, which is shown in FIG. 8. Like in FIG. 10, the "core" of this embodiment of output stage ps", which is again a complementary push-pull stage, is a series combination of the controlled current paths of a P-channel enhancement-mode insulated-gate field-effect transistor P' and an N-channel enhancement-mode insulated-gate field-effect transistor N', henceforth referred to as transistors for short.

Excitation assembly 16 is connected to the junction point of the controlled current paths. Each controlled current path is shunted by a protective diode dn', dp', with the respective cathode connected to the more positive point of the respective transistor.

The P-transistor-side end of the series combination is connected to the positive DC voltage +u, which is dependent on the output signal from comparison stage sa, and its N-transistor-side end is connected to the negative DC voltage −u, which is dependent on the output signal from comparison stage sa. The gates of transistors N', P' are connected together and to an output of a comparator kk". The noninverting input of comparator kk" is connected to the output of comparator kk, see FIG. 8.

The inverting input of comparator kk" is connected to a tap of a voltage divider consisting of a resistor r3 and a resistor r4. Resistors r3, r4 are of equal value and are connected between the constant positive first DC voltage +U1 and ground SN. Resistors r3, r4 and comparator kk" serve to balance the output signal from comparator kk with respect to half the value of the DC voltage +U1.

Thus, excitation assembly 16 receives a positive current pulse during each positive half-cycle of the output signal from sensor 17 or of the sum of the output signals from sensors 17, 18, and a negative current pulse during each negative half-cycle of the output signal from sensor 17 or of the sum of the output signals from sensors 17, 18. The respective amplitude of these current pulses is dependent on the DC voltages +u, −u, which in turn depend on the output signal from comparison stage sa, so that the vibration amplitude of the flow tube or flow tubes 1, 2 specified by reference signal Sr adjusts itself automatically.

The DC voltages +U1, +U2, −U2 are generated in the usual manner on the basis of the power made available by the two-wire process control loop. It is also possible to provide only a single positive DC voltage instead of the two positive DC voltages +U1, +U2.

In the invention, the aforementioned two-wire process control loop preferably carries a DC supply current, with the measurement signal, in particular, also being a direct current, for instance a current in the standard range of 4 to 20 mA. On the other hand, the measurement signal may also preferably be a digital signal, so that the two-wire process control loop can be connected to a field bus.

The excitation circuit of the invention and the flow tube or flow tubes 1, 2 represent an automatic control system which electrically adjusts itself both to the mechanical resonance frequency of the excited vibrations of the flow tube or of flow tubes 1, 2 and to the amplitude of these vibrations specified by reference signal Sr.

Therefore, the hitherto used excitation circuits, which comprise an amplitude control stage and a phase-locked loop (PLL) for electrically controlling the resonance frequency and the vibration amplitude, are not necessary. The conventional excitation circuits require not only a great number of components, but also much more power than is available in two-wire meters.

As the excitation circuit 20 of the invention requires only few components, the total power dissipation of the latter is virtually negligible, so that the available low power is usable nearly completely for the excitation.

While the invention has been illustrated and described in detail in the drawings and forgoing description, such illustration and description is to be considered as exemplary not restrictive in character, it being understood that only exemplary embodiments have been shown and described and that all changes and modifications that come within the spirit and scope of the invention as described herein are desired to protected.

What is claimed is:

1. A viscometer for a fluid flowing in a pipe, said viscometer comprising:
    a vibratory transducer, with at least one flow tube for conducting the fluid, and for generating friction forces acting in the fluid, the at least one flow tube communicating with the pipe and vibrating in operation, and with an excitation assembly for vibrating the at least one flow tube; and
    meter electronics which deliver an excitation current for the excitation assembly and a viscosity value representing the instantaneous viscosity of the fluid, said meter electronics being connected to, and supplied with electric power from, a two-wire process control loop, and said meter electronics feeding and controlling, respectively, a viscosity signal corresponding to the viscosity value into the two-wire process control loop.

2. The viscometer as claimed in claim 1, wherein vibratory transducer is a flexural mode transducer.

3. The viscometer as claimed in claim 1, wherein vibratory transducer is a torsional mode transducer.

4. The viscometer as claimed in claim 1, wherein vibratory transducer is a flexural and torsional mode transducer.

5. The viscometer as claimed in claim 1 wherein the electric power requirement of the meter electronics is variable, and wherein the meter electronics comprise a control circuit for adjusting the electric power requirement.

6. The viscometer as claimed in claim 5 wherein the meter electronics comprise an excitation circuit for generating the excitation current, and an evaluating circuit for registering the sensor signal and for determining the viscosity value; and wherein the control circuit temporarily deactivating the excitation circuit and/or the evaluating circuit to reduce the electric power requirement.

7. The viscometer as claimed in claim 1 wherein the meter electronics comprise an energy store coupled to the two-wire process control loop, said energy store being operable to supply said meter electronics at least in part at least temporarily.

8. The viscometer as claimed in claim 7, wherein the control circuit causes temporary charging of the energy store.

9. The viscometer as claimed in claim 1 wherein the viscometer is connected by means of the two-wire process control loop to a field bus.

10. The viscometer as claimed in claim 9 wherein the two-wire process control loop carries a direct current.

11. The viscometer as claimed in claim 10 wherein the viscosity signal is a variable direct current.

12. The viscometer as claimed in claim 10 wherein the viscosity signal is a variable direct current in a range of 4 to 20 m.A.

13. The viscometer as claimed in claim 10 wherein the viscosity signal is a digital signal.

14. The viscometer as claimed in claim 1 wherein the transducer comprises a sensor arrangement for sensing vibrations of the flow tube and for producing at least one sensor signal representing said vibrations.

15. The viscometer as claimed in claim 14 wherein the meter electronics adjust the excitation current by means of the sensor signal.

16. The viscometer as claimed in claim 14 wherein the excitation circuit comprises:
   an demodulation stage fed by the at least one sensor signal or a sum of two sensor signals, said two sensor signals being delivered by the sensor arrangement, said demodulation stage being operable to generate an output signal representing an oscillation amplitude of said vibrating tube.

17. The viscometer as claimed in claim 16 wherein the excitation circuit further comprises:
   a comparison stage fed by the output signal of the demodulation stage, said comparison stage being operable to generate an output signal representing a deviation of said oscillation amplitude of the vibrating tube from an predetermined reference oscillation amplitude for said vibrations.

18. The viscometer as claimed in claim 17 wherein the excitation circuit further comprises:
   an amplitude modulation stage for modulating said signal fed to the demodulation stage with said output signal from the comparison stage, said amplitude stage being operable to generate a drive signal for supplying said excitation assembly.

19. The viscometer as claimed in claim 17 wherein the excitation circuit further comprises:
   an pulse duration modulation stage for modulating said signal fed to the
demodulation stage with said output signal from the comparison stage, said pulse duration stage being operable to generate a drive signal for supplying said excitation assembly.

* * * * *

UNITED STATES PATENT AND TRADEMARK OFFICE
CERTIFICATE OF CORRECTION

PATENT NO. : 7,634,939 B2  Page 1 of 1
APPLICATION NO. : 10/173748
DATED : December 22, 2009
INVENTOR(S) : Drahm et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1003 days.

Signed and Sealed this

Twenty-first Day of December, 2010

David J. Kappos
*Director of the United States Patent and Trademark Office*